United States Patent
Kropf

(10) Patent No.: US 6,719,799 B1
(45) Date of Patent: Apr. 13, 2004

(54) IMPLANTABLE PROSTHESIS HAVING AT LEAST TWO SECTIONS WHICH CAN BE DISPLACED IN RELATION TO ONE ANOTHER, AND THE USE OF DISPLACEABLE SECTIONS

(75) Inventor: Philipp Kropf, Uitikon (CH)

(73) Assignee: Argomedical AG (CH)

( * ) Notice: Subject to any disclaimer, the term of this patent is extended or adjusted under 35 U.S.C. 154(b) by 0 days.

(21) Appl. No.: 09/763,996

(22) PCT Filed: Sep. 10, 1999

(86) PCT No.: PCT/EP99/06689

§ 371 (c)(1),
(2), (4) Date: Feb. 27, 2001

(87) PCT Pub. No.: WO00/15154

PCT Pub. Date: Mar. 23, 2001

(30) Foreign Application Priority Data

Sep. 11, 1998 (DE) .......................... 198 41 612

(51) Int. Cl.$^7$ ................................ A61F 2/40
(52) U.S. Cl. ................. 623/19.14; 623/19.13; 623/19.12
(58) Field of Search ............... 623/18.11, 19.11, 623/19.12, 19.13, 19.14

(56) References Cited

U.S. PATENT DOCUMENTS

| 5,314,479 A | * | 5/1994 | Rockwood et al. ...... 623/19.14 |
| 5,358,526 A | * | 10/1994 | Tornier ................. 623/19.14 |
| 6,197,063 B1 | * | 3/2001 | Dews .................... 623/19.14 |

FOREIGN PATENT DOCUMENTS

| DE | 19509037 | | 9/1996 |
|---|---|---|---|
| EP | 0 024 442 | | 3/1981 |
| EP | 0 549 480 | | 6/1993 |
| EP | 0 599 429 | | 6/1994 |
| EP | 0599429 A2 | * | 6/1994 |
| EP | 0 679 375 | | 11/1995 |
| EP | 0 712 617 | | 5/1996 |
| EP | 0 715 836 | | 6/1996 |
| EP | 0 815 810 | | 1/1998 |
| EP | 0 821 924 | | 2/1998 |
| EP | 0 903 128 | | 3/1999 |
| FR | 2 721 200 | | 12/1995 |
| WO | WO 98/04216 | | 2/1998 |
| WO | WO 98/46172 | | 10/1998 |

* cited by examiner

*Primary Examiner*—Corrine McDermott
*Assistant Examiner*—Hieu Phan
(74) *Attorney, Agent, or Firm*—Bachman & LaPointe, P.C.

(57) ABSTRACT

An implantable prosthesis having at least two portions which are displaceable relative to each other, in particular a prosthesis for the upper end of a human upper arm comprising a shaft which can be inserted into a bone passage and a dome-shaped joint head which is to be associated with the adjacent joint head and which can be connected to an end face of the shaft in an eccentric position or a neutral position relative to the center axis thereof by means of an intermediate disk which has a circular periphery and which comprises both in relation to the joint head and in relation to the shaft a respective insert pin or the like peg-shaped portion formed thereon which can be inserted into a bore, wherein the mutually displaceable portions of the prosthesis are arranged steplessly displaceably relative to each other at at least one displacement plane which is determined by the surface of a portion about axes which are determined by the insert pins of the intermediate disk.

21 Claims, 4 Drawing Sheets

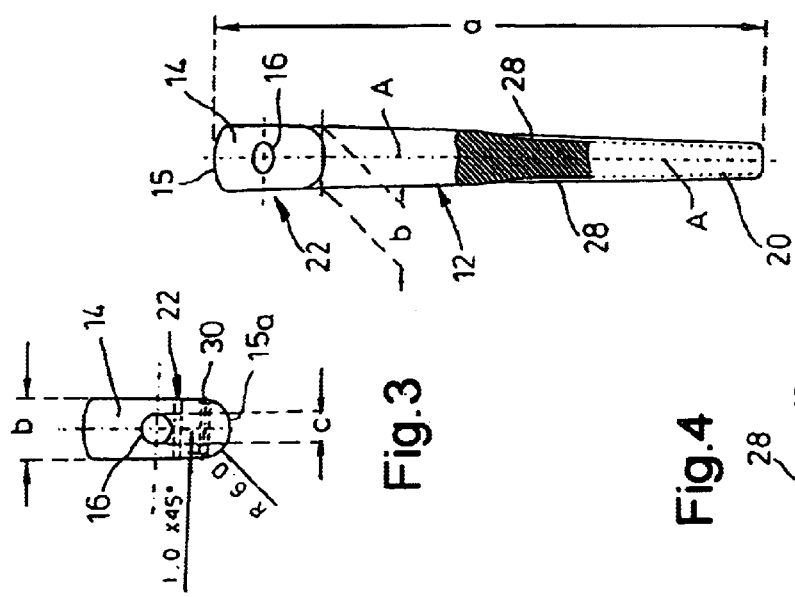
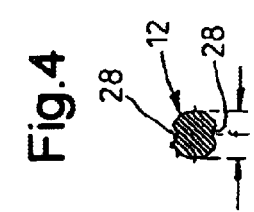
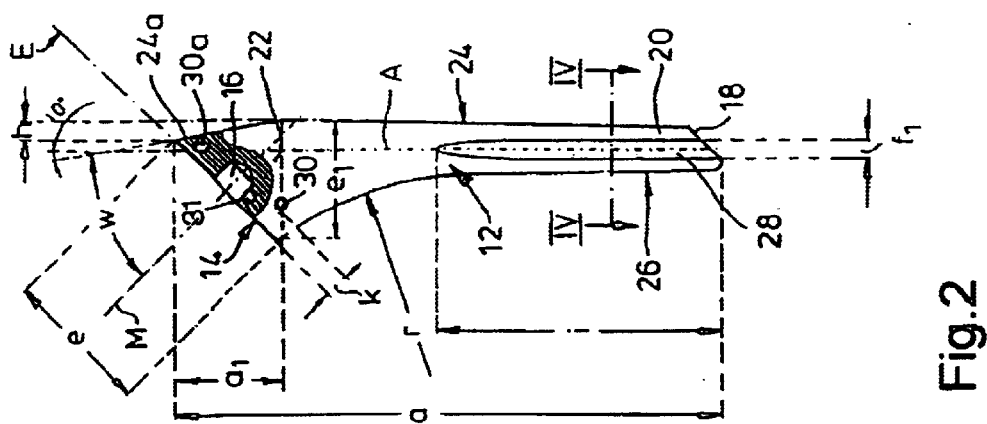
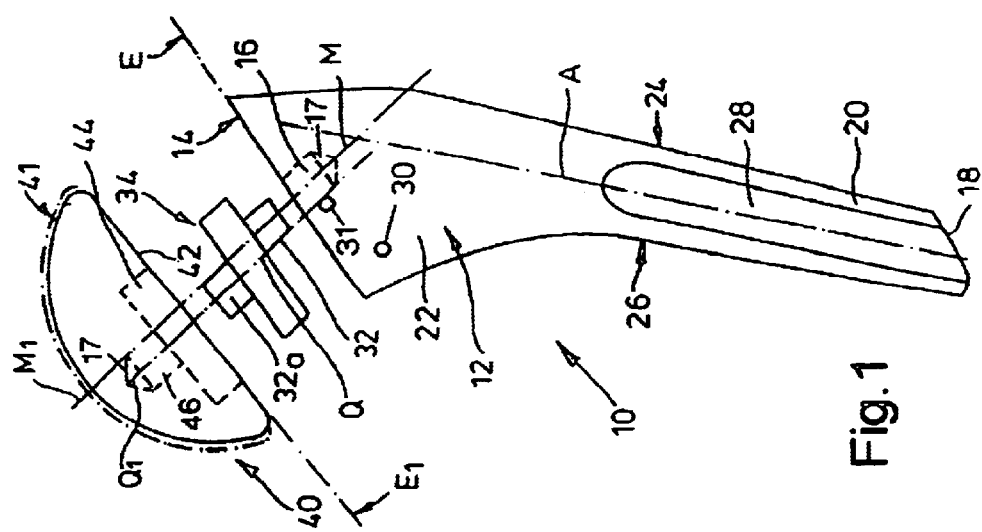
Fig.1
Fig.2
Fig.3
Fig.4
Fig.5

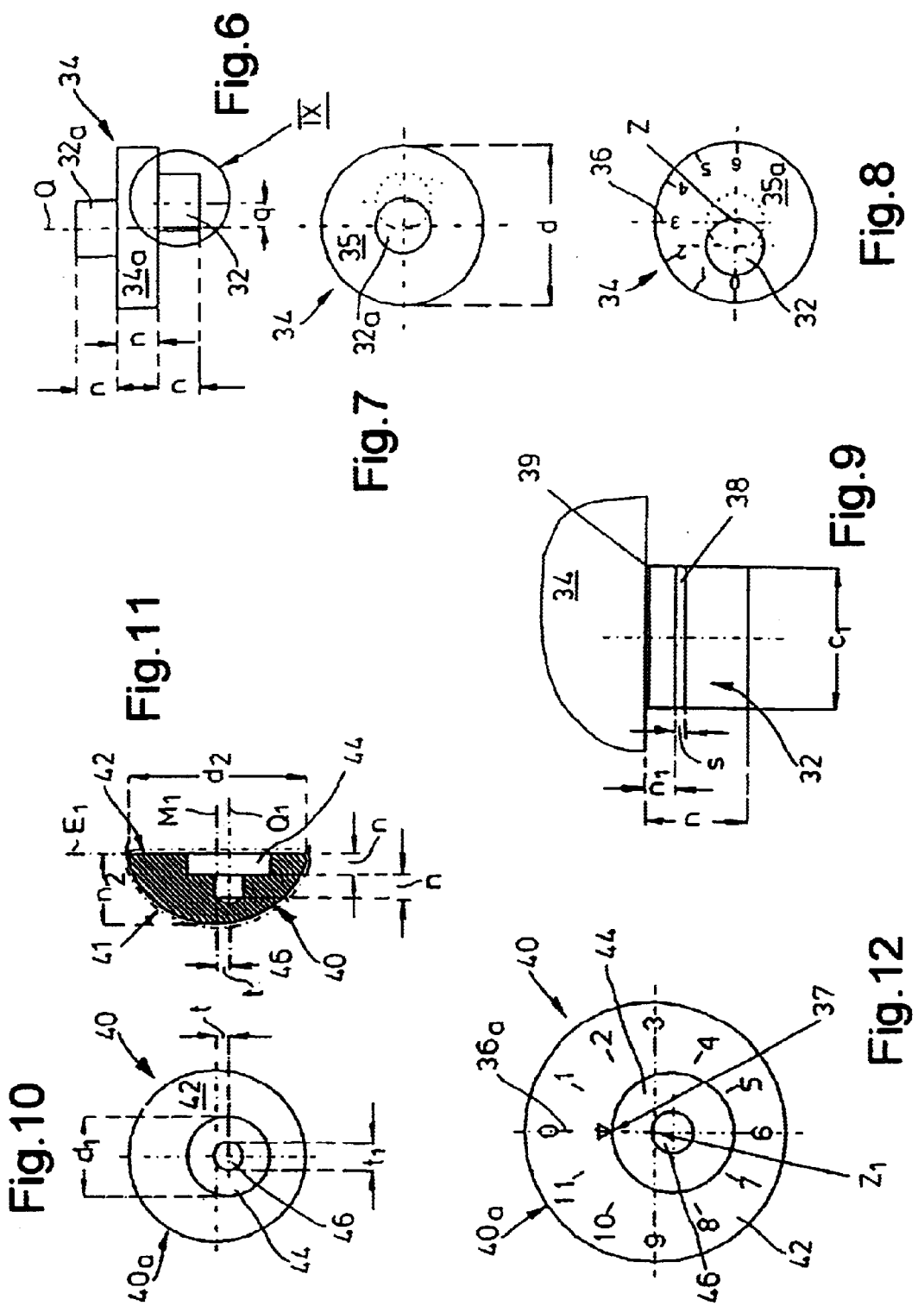

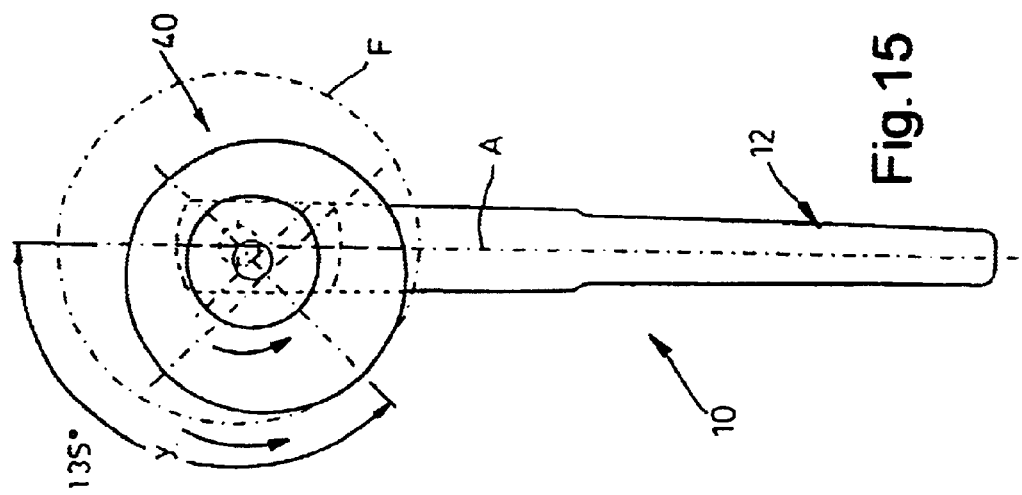
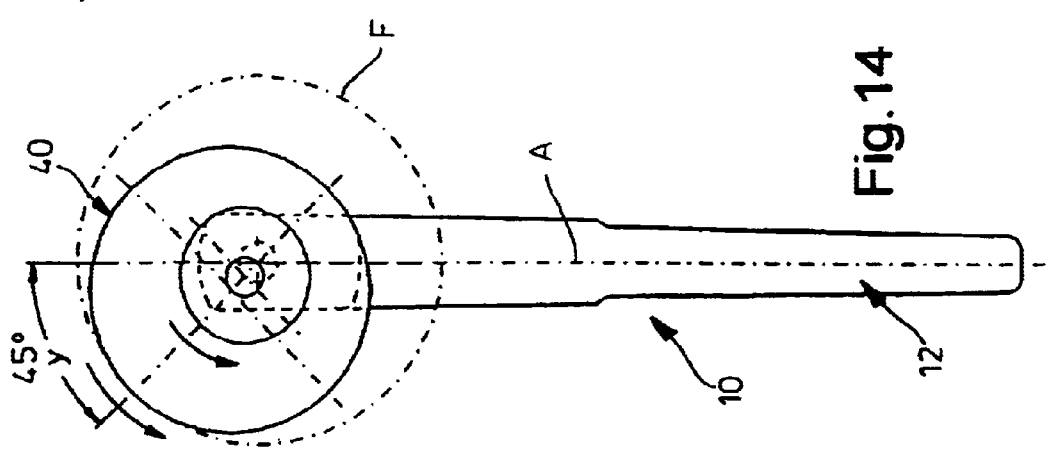
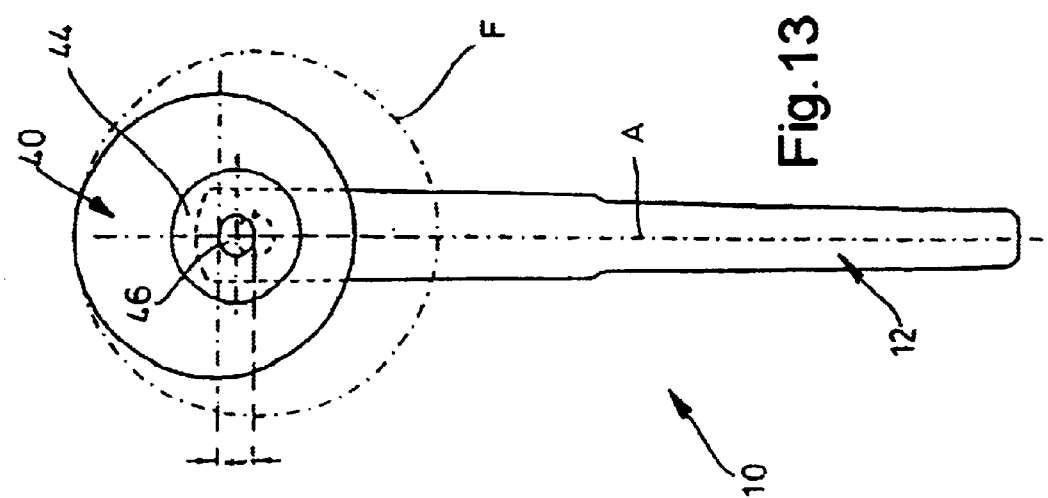

IMPLANTABLE PROSTHESIS HAVING AT LEAST TWO SECTIONS WHICH CAN BE DISPLACED IN RELATION TO ONE ANOTHER, AND THE USE OF DISPLACEABLE SECTIONS

BACKGROUND OF THE INVENTION (1). Field of the Invention

The invention comprises an implantable prosthesis having at least two portions which are displaceable relative to each other, in particular a prosthesis for the upper end of a human upper arm comprising a shaft which can be inserted into the humerus passage thereof and a dome-shaped joint head which is to be associated with the joint socket adjacent to the upper arm and which can be connected to an end face of the shaft in an eccentric position relative to the center axis thereof by means of an intermediate disk which has a circular periphery and which comprises both in relation to the joint head and in relation to the shaft a respective insert pin or the like peg-shaped portion formed thereon which can be inserted into a bore. The invention also concerns the use of displaceable portions and an intermediate disk on a displacement plane.

(2). Description of the Related Art

A joint prosthesis of that kind is to be found in EP 0 549 480 A1. A central insert pin projects from the intermediate disk at each of the two sides thereof. Provided for the insert pin at the head side is the joint head is an eccentric bore and around same a ring of smaller bores for receiving a fixing pin which is parallel to the axis and which engages both into the bore and also into the intermediate disk. Displacement of the joint or humerus head is effected stepwise and cannot therefore be adapted to the factors involved in all situations. In addition the structure of this shoulder joint prosthesis does not make it possible to displace section axes or resection axes.

EP 0 712 617 A1 also describes a joint prosthesis, in the shaft of which the joint head is supported by means of a ball joint. This also does not permit fine tuning of the joint head.

SUMMARY OF THE INVENTION

In consideration of that state of the art, the inventor set himself the aim of so designing a prosthesis of the kind referred to in the opening part of this specification that, in regard to adaptation thereof to the respective anatomical aspect of the human bones which are to be connected therewith, fine adjustment is also possible without any problem.

That object is attained by the teaching of the independent claim; the appendant claims set forth advantageous developments. Furthermore, the scope of the invention embraces all combinations of at least two of the features disclosed in the description, the drawing and/or the claims.

In accordance with the invention the mutually displaceable portions are arranged steplessly displaceably around axes relative to each other at at least one displacement plane, wherein preferably one of the insert pins is to be arranged at a radial spacing relative to the axis of the intermediate disk.

By virtue of those measures, the shaft and the joint head—or two parts which are to be correspondingly displaced of other implant prostheses—can be displaced at that end face or parallel thereto steplessly in relation to each other.

In accordance with another feature of the invention the intermediate disk—which can be inserted into an opening of the same shape as same in one of the adjacent portions—is to be fitted with a central insert pin into a corresponding opening formed eccentrically in a connection plane of the joint head; the other—eccentrically disposed—insert pin is associated with the end face of the shaft. The connection plane moreover determines one of two displacement planes of the prosthesis; the other lies in the end face of the shaft.

It has proven to be desirable for the diameter of the intermediate disk to approximately correspond to half the diameter of the joint head and for the height thereof to approximately correspond to the respective height of the insert pins thereof; for that purpose the height of the intermediate disk should be equal to approximately a third of its diameter with a preferred pin diameter whose length in relation to the diameter of its intermediate disk is in a ratio of between about 1:2.5 and 1:3.0. In addition the radial spacing of the eccentrically disposed insert pin from the axis of the intermediate disk should approximately correspond to half the pin diameter.

It will be clear that the connecting surface of the joint head according to the invention affords a shallow blind opening which is displaced out of the axis of the connecting surface, for insertion of the intermediate disk which is equipped with an insert pin on both sides thereof. The two insert pins of the intermediate disk are displaced radially relative to each other and make it possible for the joint head to be steplessly displaced with respect to the prosthesis shaft.

Preferably the insert pins are fitted as a press fit into their blind bore. For example they can each afford an annular press-fit region whose height at a tenth of the pin height is sufficient but may also be wider.

In a further embodiment the insert pin may be of a slightly tapering configuration; the conicity of the insert pin also guarantees the seating thereof in the cylindrical blind bore.

In accordance with a further feature of the invention the position of the intermediate disk is fixed by assembly thereof to the joint head or the shaft respectively.

In a specific embodiment of the invention the diameter of the insert pins can measure between 1 and 9 mm, preferably up to 7 mm. For that purpose then the intermediate or eccentric disk is of a diameter of between 10 and 35 mm—preferably between 12 and 30 mm—and a thickness of between 2 and 8 mm, preferably between 3 and 7 mm.

With dimensions of that kind, it has proven to be advantageous if the shallow opening for the intermediate disk in the dome-shaped joint head of the implantable prosthesis is displaced out of the center axis thereof by up to 10 mm, preferably up to 8 mm.

The association in accordance with the invention of two displaceable portions and the intermediate disk thereof at a displacement plane can also be used for implantable prostheses of another kind.

BRIEF DESCRIPTION OF THE DRAWINGS

Further advantages, features and details of the invention will be apparent from the description hereinafter of preferred embodiments and with reference to the drawings in which:

FIG. 1 is a diagrammatic side view of a modular shoulder joint prosthesis with an intermediate disk associated with a shaft and a joint head which can be fitted on to the intermediate disk, in the mutually separated condition, FIG. 2 shows the shaft of FIG. 1, having an end face at one end, FIG. 3 shows a plan view of the end face of the shaft, FIG. 4 is a view in cross-section through FIG. 2 taken along line IV—IV therein, FIG. 5 is a partly sectional front view of the shaft, FIG. 6 shows a side view of the intermediate disk, FIGS. 7 and 8 show plan views of the intermediate disk, FIG. 9 shows a view on an enlarged scale of a portion of FIG. 6 viewing along arrow IX therein, FIG. 10 shows a plan view of the joint head, FIG. 11 is a sectional side view of the joint head, FIG. 12 is a view on an enlarged scale in relation to FIG. 10 of a further joint head, FIG. 13 shows a front view of the shoulder joint prosthesis in a first set position, and FIGS. 14 through 17 show the shoulder joint prosthesis of FIG. 13 in other set positions of the joint head, which are different in relation to each other.

DETAILED DESCRIPTION OF PREFERRED EMBODIMENT(S)

Figure 17:
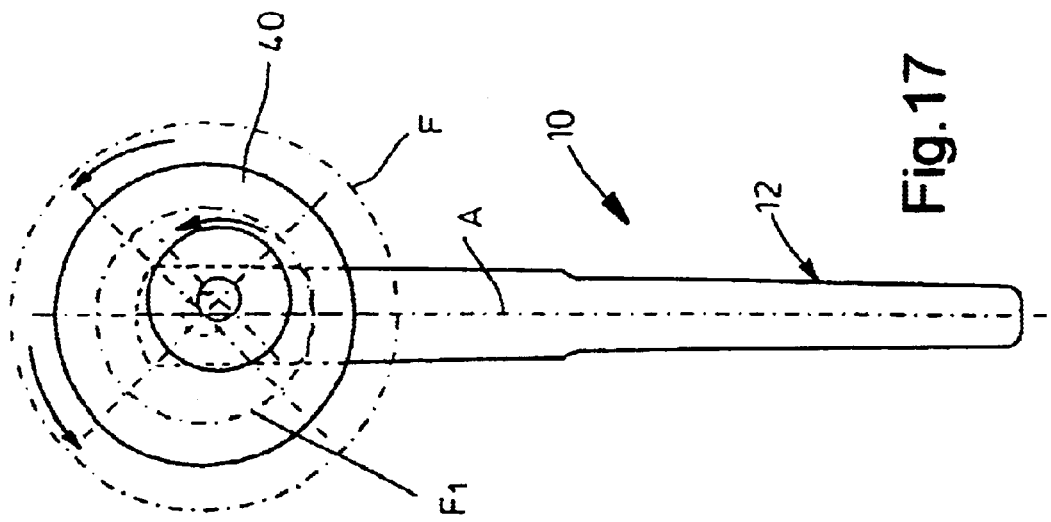

A prosthesis 10 for a human shoulder joint (not shown) comprises a shaft 12 with an end face 14 whose center axis M is inclined relative to the longitudinal axis A of the shaft 12 at an angle w of 45°. The greatest length a of the shaft 12 measures 125 mm, the width b of the end face 14 measures about 14 mm and the length e thereof measures about 23 mm. The projection length e', which can be seen in FIG. 2, of the end face 14 into a plane which crosses the longitudinal axis A at a right angle is then 27.3 mm.

The center axis M of the end face 14 determines therein the position of a blind hole 16 of a diameter d of about 7 mm with a conical end 17. Opposite the free shaft end—which terminates at a suitable base surface 18—of a width f of 11 mm the head region 22 of the shaft 14 is enlarged to the length e or $e_1$. The upper, slightly rounded narrow edge 15 of the end face 14 is displaced with respect to a condition of alignment with the side 24 of its shaft by virtue of an inclination region 24a provided in the latter, of a length $a_1$ parallel to the axis of about 25 mm, such displacement being by a dimension h of about 4.5 mm; the other side 26 of the shaft is curved outwards at a radius r=70 mm towards the second narrow edge $15_a$ of the end face 14. Extending in the region of the shaft which remains approximately the same in terms of cross-section at both sides thereof are central shallow grooves 28 of a width $f_1$ of in this case 4.6 mm and a length i of 65 mm.

At a spacing k of about 5.5 mm, a transverse bore 30 passes through the head region 22 of the shaft 12 near the side 26 of the shaft, which is curved with the radius r; indicated at $30_a$ in FIG. 2—also at a spacing relative to the blind hole 16—is a possible further transverse bore, in the proximity of the upper narrow edge 15 of the end face 14. Reference 31 denotes a tangential bore to the blind hole 16 for a screw for fixing the pin fitting.

The blind hole 16 of the end face 14 serves to receive an insert pin or peg 32—of a suitably round cross-section of a diameter $c_1$ of 7 mm—on an intermediate or eccentric disk 34 of a diameter d of 20 mm and a height n of 5 mm, which is provided on both sides with such an insert pin 32, $32_a$ of equal height n; the insert pin 32 which is towards the shaft is radially displaced at a spacing q of 3 mm in respect of its axis relative to the center axis Q of the eccentric disc 34, while the second insert pin $32_a$ projects axially from the disk face 35. Depending on the design configuration involved the spacing q can measure between 1 mm and 10 mm, preferably up to 8 mm.

FIG. 8 shows a scale 36 with marking lines on the disk face $35_a$, the scale 36 being oriented with respect to the disk center Z, while FIG. 9 shows the eccentric insert pin 32 with an annular press-fit region 38 of a width s of 0.5 mm which is at a spacing $n_1$ of 1.5 mm from the other disk face $35_a$ of the eccentric disk 34 adjoining the insert pin 32 above an undercut or relief groove 39. The eccentric disk 34 is used in two variants, more specifically on the one hand with the illustrated press fit for both insert pins 32, $32_a$ which taper slightly conically towards the end (not shown) or on the other hand, entirely without a press fit. The above-mentioned transverse bore 30 can receive a locking screw (not shown) for increasing the clamping force of the shaft.

The eccentric insert pin $32_a$ is intended for connection to the dome-shaped humerus or joint head 40 which at a connecting surface 42 affords for the eccentric disk 34 an opening 44 corresponding to the shape thereof, of a diameter $d_1$, with an eccentric blind bore 46 for the insert pin $32_a$. Here, the axis $Q_1$ of the bore is at a spacing t of 3 mm relative to the center axis $M_1$ of the joint head 40 and the center axis $M_1$ of the eccentric disk 34 goes into the cylindrical wall of the eccentric bore 46 of the opening 44. In this case also the spacing t, depending on the respective design configuration involved, may suitably range between 1 mm and 10 mm, preferably up to 8 mm.

The height $n_1$ of the dome portion, which has a polished surface 41, of the joint head 40 is preferably proportional to the diametral length of the surface in the form of a portion of a sphere and measures for example somewhat more than 17 mm, while the diameter $d_2$ of the joint head 40 here measures somewhat more than 44 mm.

As shown in FIG. 12 the connecting surface 42 also has a scale $36_a$ which is oriented to the center Z thereof, and in addition a marker triangle 37 at the edge of the opening 44.

FIGS. 13 through 17 show the different set positions of the joint head 40 on the shaft 12 by virtue of the eccentricity which is possible by means of the eccentric disk 34, wherein E and $E_1$ denote the displacement planes which are defined by the end face 14 of the shaft 12 and the connection plane 42 of the joint head 40—and which are away from each other in the position of installation—and F and $F_1$ denote contour circles for the contour $40_a$ of the joint head 40 and the contour $34_a$ of the eccentric disk 34 respectively.

Figure 16:
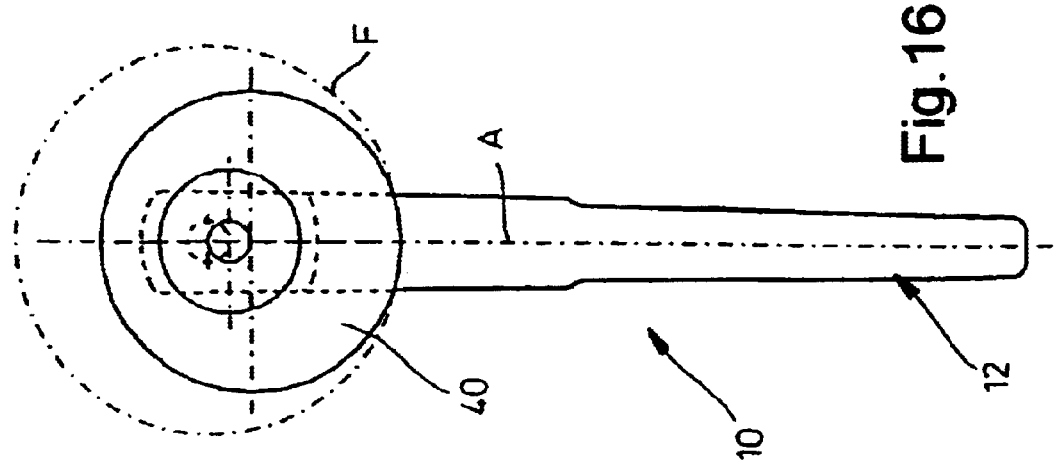

FIG. 13 shows the maximum outward eccentricity with in this case t=6 mm. With a simultaneous rotary movement through a displacement angle y through 45° as shown in FIG. 14 and through 135° as shown in FIG. 15 of the eccentric disk 34 and the joint head 40, positions are occupied on the circle F—with simple eccentricity. The maximum inward eccentricity is achieved as shown in FIG. 16 after a displacement angle of 180°.

The possibility of steplessly rotating the eccentric disk 34 independently of the joint head 40 means that it is possible to go to an unlimited plurality of positions. It is possible to set any position within the two circles F, $F_1$ in FIG. 17; that Figure shows the complete zero position, in other words the joint head 40 is disposed concentrically in the circles E, $E_1$. In FIGS. 13 and 16 the longitudinal axis A of the shaft 12 forms a straight line of symmetry.

What is claimed is:

1. An implantable prosthesis having at least two portions which are displaceable relative to each other, in particular a prosthesis for the upper end of a human upper arm comprising a shaft which can be inserted into a bone passage and a dome-shaped joint head which is to be associated with the adjacent joint head and which can be connected to an end face of the shaft said dome-shaped joint head sized and configured to assume a plurality of eccentric positions and sized and configured to assume a neutral position relative to the center axis thereof by means of an intermediate disk which has a circular periphery and which comprises both in relation to the joint head and in relation to the shaft a respective insert pin or the like peg-shaped portion formed thereon which can be inserted into a bore, wherein the mutually displaceable portions of the prosthesis are arranged steplessly displaceably relative to each other at at least one displacement plane which is determined by the surface of a portion about axes which are determined by the insert pins of the intermediate disk.

2. A prosthesis as set forth in claim 1 wherein at least one of the insert pins is arranged at a radial spacing relative to the axis of the intermediate disk.

3. A prosthesis as set forth in claim 2 wherein the diameter of the intermediate disk corresponds approximately to half the diameter of the joint head and its height approximately corresponds to the respective height of the insert pins thereof.

4. A prosthesis as set forth in claim 3 wherein the height of the intermediate disk approximately corresponds to a third,of its diameter.

5. A prosthesis as set forth in claim 3 wherein a pin diameter whose length in relation to the diameter of its intermediate disk is in a ratio of between approximately 1:2.5 and 1:3.0.

6. A prosthesis as set forth in claim 2 wherein the radial spacing of the eccentrically disposed insert pin from the axis of the intermediate disk approximately corresponds to half the pin diameter.

7. A prosthesis whose intermediate disk can be inserted into an opening approximately corresponding thereto in one of the adjacent portions, as set forth in claim 1, wherein the intermediate disk is fitted with a central insert pin into an opening which corresponds to the configuration thereof and which is formed eccentrically in a connecting surface of the joint head and the other eccentrically mounted insert pin is associated with the end face of the shaft, and wherein the connecting surface determines a displacement plane of the prosthesis.

8. A prosthesis as set forth in claim 1 wherein the insert pin has an annular press-fit region.

9. A prosthesis as set forth in claim 8 wherein the height of the press-fit region approximately corresponds to between a tenth and three tenths the pin height.

10. A prosthesis as set forth in claim 1 wherein the insert pin for the cylindrical blind bore tapers conically away from the intermediate disk.

11. A prosthesis as set froth in claim 1 wherein the diameter of the insert pin measures between 1 and 9 mm.

12. A prosthesis as set forth in claim 1 comprising a tangential bore for a tangential screw at the blind bore.

13. A prosthesis as set forth in claim 1 wherein the intermediate disk is of a thickness of between 10 and 35 mm.

14. A prosthesis as set forth in claim 1 wherein the shallow opening for the intermediate disk in the joint head is displaced out of the center axis thereof by up to 10 mm.

15. A prosthesis as set forth in claim 1 wherein the disk surface of the intermediate disk and/or the connecting surface of the joint head is/are provided with a scale associated with the direction of rotation.

16. Use of the association of displaceable portions and an intermediate disk at a displacement plane, as set forth in claim 1 for an elbow, knee or hip joint prosthesis.

17. Use of the association of displaceable portion and an intermediate disk at a displacement plane, as set forth in claim 1 for a hand or ankle joint prosthesis.

18. Use of the association of displaceable portion and an intermediate disk at a displacement plane, as set forth in claim 1 for an a spinal column disk prosthesis.

19. A prosthesis as set froth in claim 1 wherein the diameter of the insert pin measures between 3 and 7 mm.

20. A prosthesis as set forth in claim 1 wherein the intermediate disk is of a thickness between 3 and 7 mm.

21. A prosthesis as set forth in claim 1 wherein a shallow opening for the intermediate disk in the joint head is displaced out of the center axis thereof by up to 8 mm.

* * * * *